(12) United States Patent
Miner et al.

(10) Patent No.: US 8,523,829 B2
(45) Date of Patent: Sep. 3, 2013

(54) INTRAVENOUS DELIVERY SYSTEM

(75) Inventors: Tom Minh Miner, Riverton, UT (US);
Peter Hartl, Hengersberg (DE);
Angelika Christoph, Deggendorf (DE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1731 days.

(21) Appl. No.: 10/768,760

(22) Filed: Jan. 29, 2004

(65) Prior Publication Data
US 2005/0171491 A1   Aug. 4, 2005

(51) Int. Cl.
*A61M 1/00* (2006.01)
*A61M 5/14* (2006.01)

(52) U.S. Cl.
USPC .......................... 604/251; 604/126

(58) Field of Classification Search
USPC .................. 604/126, 251, 257, 405
See application file for complete search history.

(56) References Cited

U.S. PATENT DOCUMENTS

| | | | |
|---|---|---|---|
| 2,129,983 A | 9/1938 | Bacon | |
| 2,729,212 A | 1/1956 | Butler | |
| 3,030,954 A | 4/1962 | Thornton, Jr. | |
| 3,744,492 A | 7/1973 | Leibinsohn | |
| 3,756,233 A | 9/1973 | Goldowsky | |
| 3,931,818 A | 1/1976 | Goldowsky | |
| 4,013,072 A | 3/1977 | Jess | |
| 4,198,971 A | 4/1980 | Noiles | |
| 4,200,095 A | 4/1980 | Reti | |
| 4,243,032 A | 1/1981 | Howell | |
| 4,248,223 A | 2/1981 | Turner et al. | |
| 4,269,222 A | 5/1981 | Palti | |
| 4,413,990 A | 11/1983 | Mittleman | |
| 4,428,743 A | 1/1984 | Heck | |
| 4,465,479 A * | 8/1984 | Meisch | 604/251 |
| 4,521,212 A | 6/1985 | Ruschke | |
| 4,548,600 A | 10/1985 | Ruschke | |
| 4,571,244 A * | 2/1986 | Knighton | 604/118 |
| 4,583,979 A | 4/1986 | Palti | |
| 4,601,712 A | 7/1986 | Cole et al. | |
| 4,685,912 A | 8/1987 | Jones | |
| 4,842,588 A | 6/1989 | Jones | |
| 4,952,210 A * | 8/1990 | Alchas | 604/251 |
| 5,102,400 A | 4/1992 | Leibinsohn | |
| 5,195,987 A | 3/1993 | Karpiak | |
| 5,423,346 A | 6/1995 | Daoud | |
| 5,489,385 A | 2/1996 | Raabe et al. | |
| 5,681,294 A | 10/1997 | Osborne et al. | |

(Continued)

FOREIGN PATENT DOCUMENTS

CA   2 460 251 A1   4/2003
DE   41 42 625 A 1   4/1993

(Continued)

*Primary Examiner* — Kevin C Sirmons
*Assistant Examiner* — Bradley Osinski
(74) *Attorney, Agent, or Firm* — Cozen O'Connor

(57) ABSTRACT

An intravenous system includes an assembly for coupling a solution container to a delivery system drip chamber used for regulating the flow rate of solution in a patient intravenous line. In one embodiment, the solution delivery system includes a drip chamber having an opening formed in a side wall, and a vent plug disposed in the opening for providing a self-priming function to the IV system. A termination end of the patient intravenous line includes an end cap with a vent and a seal for allowing air in the intravenous line to escape through the end cap while preventing leakage of solution from the termination end.

32 Claims, 5 Drawing Sheets

(56) References Cited

U.S. PATENT DOCUMENTS

| | | |
|---|---|---|
| 5,735,826 A | 4/1998 | Richmond |
| 5,776,109 A | 7/1998 | Urrutia |
| 5,779,674 A * | 7/1998 | Ford .................. 604/126 |
| 5,851,202 A | 12/1998 | Carlsson |
| 5,902,281 A | 5/1999 | Kraus et al. |
| 6,099,512 A | 8/2000 | Urrutia |
| 6,106,504 A | 8/2000 | Urrutia |
| 6,149,631 A | 11/2000 | Haydel, Jr. |
| 6,213,986 B1 * | 4/2001 | Darling, Jr. .................. 604/248 |
| 6,224,578 B1 | 5/2001 | Davis et al. |
| 6,261,267 B1 | 7/2001 | Chen |
| 6,336,916 B1 * | 1/2002 | Bormann et al. .................. 604/251 |
| RE38,145 E | 6/2003 | Lynn |
| 6,833,488 B2 * | 12/2004 | Bucevschi et al. ............ 604/368 |
| 2004/0254542 A1 | 12/2004 | Sacco |
| 2005/0273062 A1 | 12/2005 | Franksson et al. |

FOREIGN PATENT DOCUMENTS

| | | |
|---|---|---|
| EP | 0 001 114 | 3/1979 |
| EP | 1 181 065 B1 | 2/2002 |
| GB | 2 044 620 | 10/1980 |
| JP | 10-127778 | 5/1998 |
| JP | 2000-014745 | 1/2000 |
| JP | 2000-229126 | 8/2000 |
| WO | WO 96/29104 | 9/1996 |
| WO | PCT/EP98/06945 | 11/1998 |
| WO | WO 99/22787 | 5/1999 |
| WO | WO 03/028525 | 4/2003 |

* cited by examiner

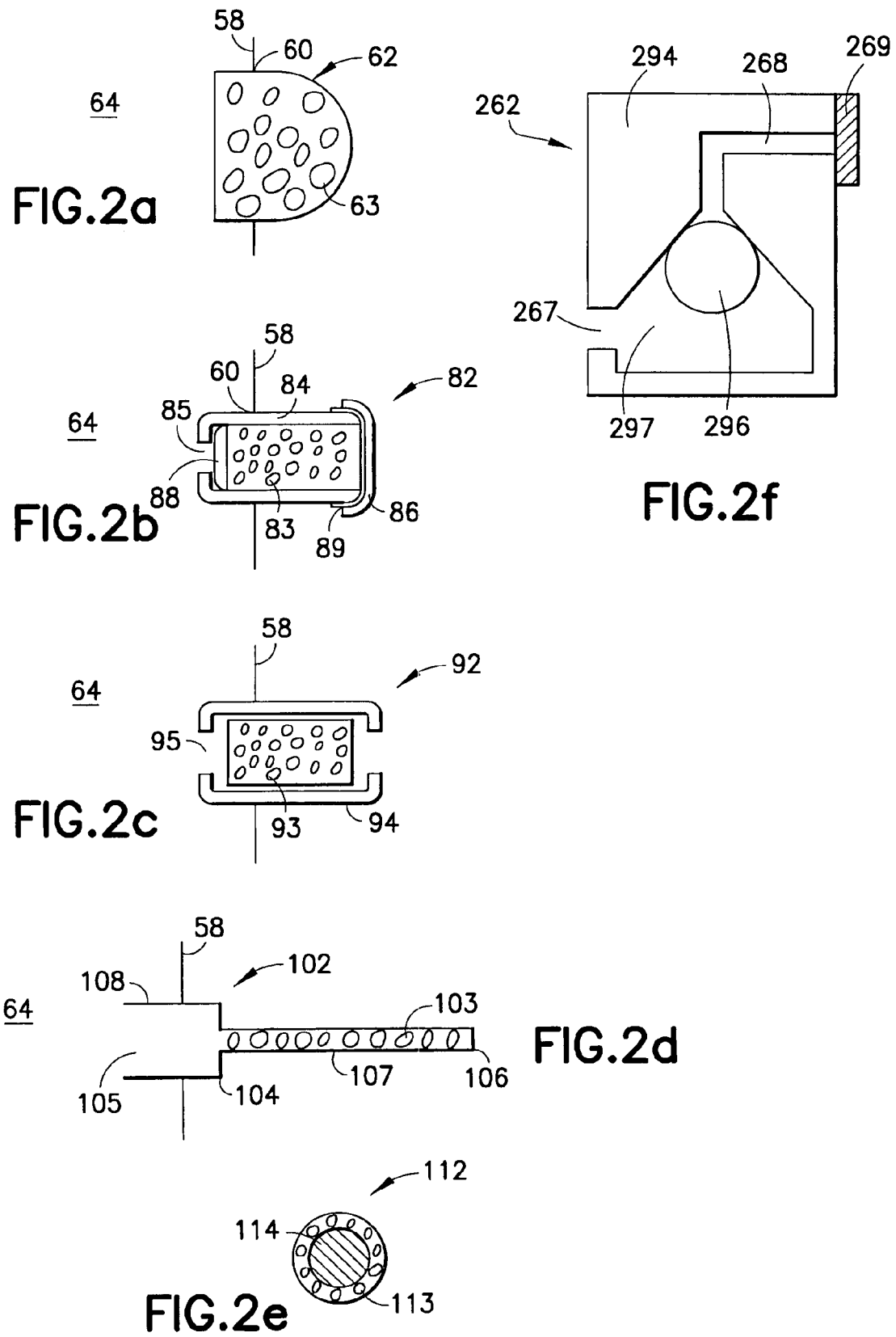

INTRAVENOUS DELIVERY SYSTEM

BACKGROUND OF THE INVENTION

1. Field of the Invention

The present invention is directed to a system for delivering liquid to patients intravenously. More particularly, the present invention pertains to an intravenous solution delivery system having a self-priming drip chamber. The present invention is also directed to an intravenous delivery system having a venting end cap to allow air present in an intravenous line to be removed.

2. Description of the Related Art

Medical liquid delivery systems are used by medical personnel to inject nutrients and/or medication into a patient's body. "Medical liquid delivery systems," as used herein, include, for example, any system for delivering an intravenous solution such as glucose, saline solution, medical dyes, and medication in liquid form, to a patient. Such systems are used during surgery or when a patient is otherwise unable to ingest nutrients or medication orally.

Intravenous liquid delivery systems ("IV systems"), for example, generally include a bottle, bag or other container of intravenous liquid that is connected by a piercing assembly or "spike" through a series of conduits to a needle or cannula inserted into a vein in the patient. The bag or container is hung from a support at a higher elevation than the patient so that intravenous solution, such as liquid medicament flows through the conduits by the force of gravity. The piercing assembly provides liquid drawn out from the container to a drip chamber directly connected to the spike assembly. As a result, the drip chamber is positioned at a height above the patient. The drip chamber is made of a transparent or translucent material so that the "drip" (i.e. the solution flow rate into the drip chamber) can be visually inspected by medical personnel monitored by an electronic drop counter.

One or more valves are disposed within the system to control the intravenous liquid flow rate in the conduit connected to the patient. Knowing the drip rate and the size of each drop, the flow rate of the infused solution can be calculated. The IV system is connected to the patient and then the flow rate is set by adjusting the valve(s).

The drip chamber is constructed of a flexible material which forms a cylindrical chamber having a top inlet port directly connected to the spike assembly, and a bottom outlet port connected to the conduit leading to the needle, i.e. "the patient line". A flow controller such as a roller clamp mounted to the outlet port conduit is used to adjust or throttle the liquid flow in the patient line by constricting or opening the outlet port conduit to adjust the flow rate. The inlet and outlet ports enclose opposite ends of a generally-cylindrical column of the drip chamber, and medicament drips from the inlet downwardly through the column where it collects at the bottom of the column and exits via the outlet.

If an infusion pump is used instead of a drip chamber, the infusion pump directly controls the IV-solution flow rate. If a drip chamber is used, however, the drip chamber must be "primed". This typically involves allowing the drip chamber to be filled to a certain level to form a reservoir, e.g., ⅓ of the drip chamber volume, with the remaining ⅔ of the volume used to visually inspect the flow rate so that the number of drops can be counted over a period of time. In certain existing drip chambers, a "fill line" is provided on the drip chamber wall to visually indicate a level corresponding to the desired ⅓ volume amount. To allow the drip chamber to fill to the desired level, the roller clamp is closed off and the drip chamber is compressed by manually squeezing the chamber to remove air therefrom. The creation of a vacuum in the drip chamber as the walls return to a non-compressed state causes medicament to be drawn into the chamber from the medicament container.

One problem with such a priming technique is that if the drip chamber is squeezed too hard such that an excessive amount of air is removed, the reduced volume will be filled by an excess amount of medicament. In that case, the drip chamber will need to be emptied so that a visual drip region can be established for counting the drops of IV-solution. The emptying of the drip chamber takes additional time and may increase the risk of line contamination that may result in a nosocomial infection to the patient. This task is typically performed by disconnecting the medicament container from the drip chamber and then opening the roller clamp to allow the liquid in the drip chamber to drain through the patient line. This task is further complicated as a result of the direct connection between the drip chamber and the spike assembly. Such direct connection provides little or no maneuverability of the drip chamber because such manipulation may cause a disturbance of the connection between the spike assembly and the medicament container. On the other hand, if the drip chamber is squeezed too delicately so that not enough air is expelled, and consequently, only a small amount of liquid fills the drip chamber to form the reservoir, the drip chamber will need to be compressed a second (and perhaps even a third) time until the reservoir reaches an acceptable level.

Another problem with existing IV systems is that when the drip chamber is squeezed to adjust the solution flow rate, the pressurized conditions in the drip chamber cause the infused liquid to flow as a narrow stream into the drip chamber at a high velocity. As the high velocity liquid stream impinges the reservoir surface, bubbles are entrapped in the reservoir, thus causing an air-bubble mixture to form. When this occurs, a time-consuming task must be performed to purge the air bubbles from the drip chamber and from the conduit leading to the patient. This typically involves gently tapping the drip chamber and the conduit leading to the patient. If air bubbles are not purged, they may enter the patient and cause an embolism or other harmful effects. Unwanted air bubbles may also be formed from a rapid filling of IV-solution into the conduit leading to the patient in infusion pump systems (e.g., when no drip chamber is present). Such air bubbles are formed on the inside surface of the conduit and are typically removed by gently tapping the conduit.

These drawbacks reduce the efficiency in which IV systems can be connected to patients when, especially in emergency conditions, time may be of the essence. Efficiency is also important to reduce the time spent by health care professionals in setting up such IV systems, thereby according such professionals more time to tend to other patients or perform other tasks.

SUMMARY OF THE INVENTION

The present invention is directed to an intravenous solution delivery system for delivery of solution such as medicament from a container, such as a bottle or a collapsible bag to a patient conduit connected to an intravenous needle or cannula in a patient. The inventive intravenous delivery system is designed to facilitate removal of air from a patient line connectable to a patient and to perform a self-priming function of a drip chamber. As used herein, the term "medicament" generally refers to intravenous-dispensed solutions.

In accordance with one embodiment, a self-priming IV-solution delivery system is disclosed for intravenous delivery of a solution from a container to a patient when the container is disposed at a height above the patient. The delivery system includes a coupling assembly connected or in communication with the container to provide flow of the solution. A drip chamber having a bottom wall and a side wall is coupled to the coupling assembly to receive solution drops formed from the flow of the solution. The drops form a reservoir in the drip chamber. The side wall of the drip chamber includes an opening located at a height above the bottom wall, and a vent plug is provided for covering the opening. The vent plug allows air contained in the drip chamber which becomes displaced upon formation of the reservoir to escape from the drip chamber through the vent plug. A patient conduit is coupled to the drip chamber output and has a termination end attachable to an intravenous needle of the patient for receiving a flow of solution from the reservoir. The patient conduit includes a flow restriction device to restrict the flow of air and liquid in the patient conduit, thereby allowing the reservoir to attain a level at least equal to the height of the vent plug while air in the patient conduit is expelled from the termination end. Wetting of the vent plug by the reservoir prevents entry of air through the vent plug to the drip chamber and prevents the exit of solution from the drip chamber through the vent plug.

In accordance with one embodiment, the vent plug is made from or includes a super-absorbent polymer.

In accordance with another embodiment, the vent plug is formed of a mechanical valve.

In accordance with another embodiment, a drip chamber is described for use in a self-priming IV-solution delivery system for intravenous delivery of a solution from a container to a patient. The delivery system includes a coupling assembly having an input and an output and configured, at its input, for coupling to the container to provide flow of the solution through the coupling assembly output. The delivery system also includes a patient conduit line for providing solution from the container to the patient. The drip chamber includes a top wall, a bottom wall, a side wall, an input and an output, and is coupled, at its input, to the coupling assembly output to receive solution drops formed from the flow of the solution for creating a reservoir defined between the bottom wall and side wall. The drip chamber side wall has an opening located at a height between the top wall and bottom wall, and a vent plug covering the opening. The vent plug allows air contained in the drip chamber which becomes displaced upon formation of the reservoir to escape from the drip chamber through the vent plug and prevents air from entering the drip chamber through the vent plug and medicament from exiting the drip chamber through the vent plug upon wetting of the vent plug by the reservoir.

According to one embodiment, the drip chamber vent plug may be integrally formed with, but of a different material than, the side wall. Alternatively, the vent plug can be configured as a band of material disposed about the side wall and over the opening.

According to another embodiment, an IV-solution delivery system is described having a coupling assembly configured for coupling to a container of solution to remove solution from the container, a patient conduit for providing the removed solution to a patient, and means for regulating a flow rate of solution from the coupling assembly to the patient conduit. The patient conduit is coupled at one end to the regulating means and has a termination end. A termination end cap is provided at the termination end of the patient conduit. The end cap has a vent for restricting the flow of solution into the patient conduit and allows air displaced by the flow of solution in the patient conduit to escape through the termination end. The end cap also includes a termination end vent plug for preventing the escape of solution through the termination end cap upon wetting of the vent plug by the solution.

In accordance with another embodiment, a method for connecting an IV-solution delivery system to a patient is provided. The method includes disposing a container of solution at a height above the patient, attaching a coupling assembly to the container for providing flow of the solution from the container, coupling a drip chamber having an opening in a side wall, and a vent plug disposed over the opening, to the coupling assembly to receive solution drops formed from the flow of the solution. The method also includes the steps of connecting a patient conduit to the drip chamber output, restricting the flow of solution in the patient conduit to a rate below the rate of solution entering the drip chamber to allow a solution reservoir defined between a bottom wall and a side wall to form to a height for wetting the vent plug, connecting a termination end of the patient conduit to the patient once the vent plug is wet from the reservoir and air is removed from the patient conduit, and discontinuing the restriction step upon wetting of the vent plug by the reservoir and removal of air from the patient conduit.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings,

FIGS. 2a-2f depict embodiments of a vent plug for use in the IV system of FIG. 1;

DETAILED DESCRIPTION OF THE PRESENTLY PREFERRED EMBODIMENTS

Figure 1:
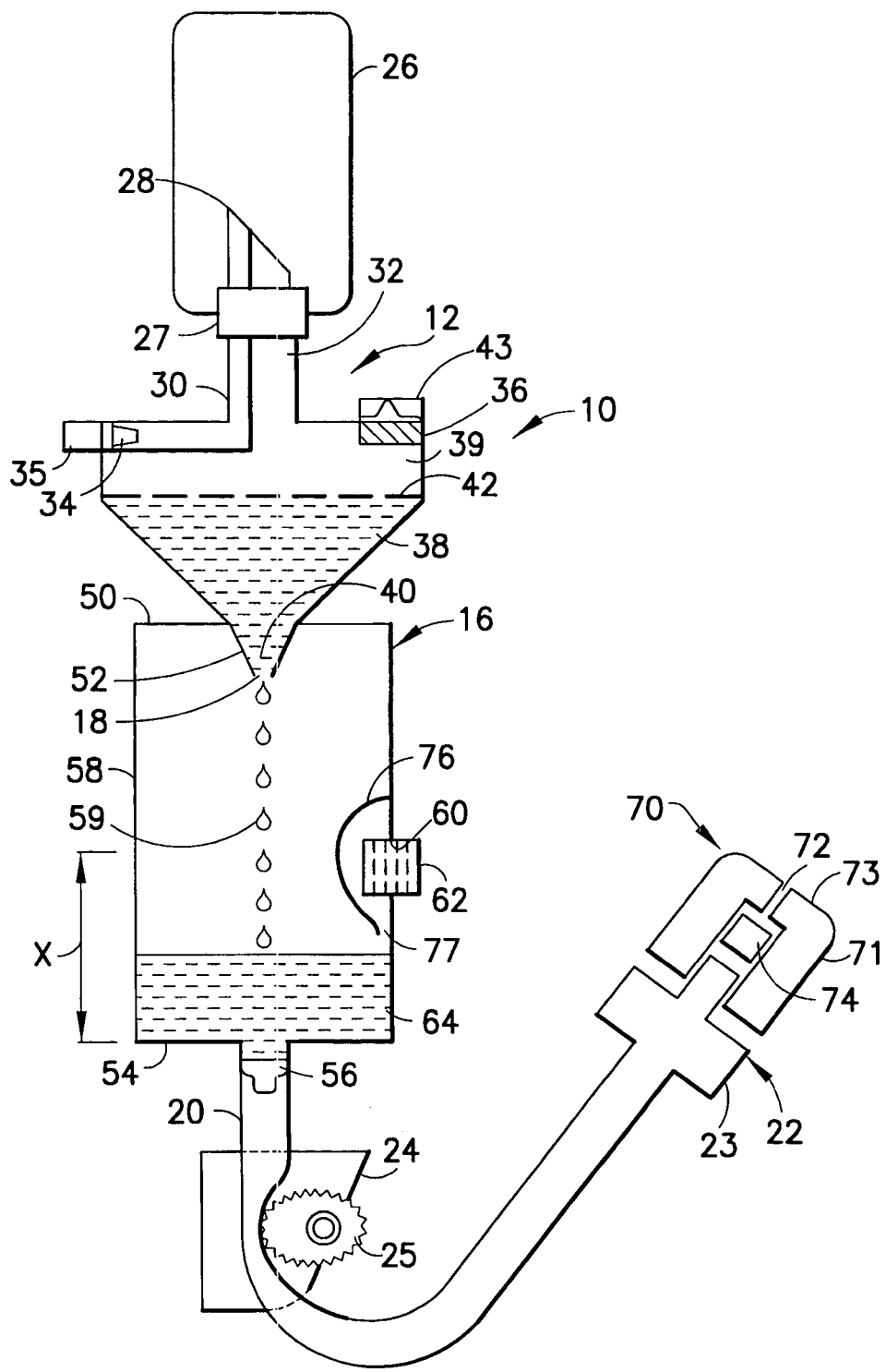
FIG. 1 is a schematic depiction of a self priming IV solution delivery system in accordance with a preferred embodiment of the present invention.

FIG. 1 depicts a self priming IV delivery system 10 used for administering a IV-solution through a vein of a patient. As used herein, the terms "IV-solution", "solution" and "medicament" are intended to refer to any substance that may be administered intravenously to a patient. The solution is located in a container 26 such as a vented rigid container or bottle, or a collapsible plastic bag, as is known in the art. The IV system 10 is a hermetically sealed system and includes a solution coupling spike assembly 12 having a lancing or piercing member 28 for piercing a seal 27 on the container 26. Other primary components of the IV system 10 include a drip chamber 16, and a patient conduit or line 20 having a termination end 22 and supporting a flow controller such as a roller clamp 24 for controlling the flow of liquid medicament in the patient line 20.

Spike assembly 12 can be of various configurations as is well known to those of ordinary skill in the art. Preferably, the spike assembly 12 used in the inventive IV system 10 is of the type described in EP application No. 1 181 065 B1 titled "Infusion Apparatus" owned by BD Infusion Therapy GmbH, and includes a hollow piercing end 28 for insertion into the container 26, a venting conduit 30 and a liquid conduit 32. The venting conduit 30 provides a sealable opening at an outer end for communicating with the surrounding atmosphere, i.e. with the environment in which the IV system 10 is disposed. When the spike assembly 12 is connected to a rigid container 26, such as a glass bottle, venting of the container is provided through the conduit 30 to allow the liquid to flow. If, on the other hand, the container 26 is a collapsible bag, venting is not required and the conduit 30 can remain sealed. As the liquid medicament is drawn out by the piercing member 28 of the spike assembly 12, the liquid flows down into a funnel-shaped portion 38 having an outlet end 40 which supports a drip orifice 18 or which otherwise directs the medicament to the drip orifice for providing the medicament, in the form of a succession of individual drops 59, to the drip chamber 16. The piercing member 28 and spike funnel portion 38 are preferably molded of a plastic material such as acrylonitrile butadiene styrene (ABS).

The spike assembly 12 also includes a check valve 34 disposed at an outlet end of the venting conduit 30 and an air filter 35 disposed between the check valve 34 and the surrounding atmosphere, as shown. When the venting conduit is opened, as in the case of the piercing member 28 being coupled to a rigid container 26, the check valve allows filtered air, through air filter 35, to enter the venting conduit to cause liquid to flow out of the container, but prevents air, and consequently, liquid, from exiting the container 26 through the venting conduit 30. A membrane 42 configured as a fine mesh screen is also preferably included in the spike assembly 12. The membrane may be formed of any suitable material—such as polyamide nylon 6,6, polyamide nylon 11, or polyester-polyethelene teraphthalate with a hydrophilic coating applied by a plasma coating process—and causes a sealing off of the funnel portion 38 of the spike assembly from the fluid conduit 32 when the contents of the container 26 have been drained into the spike assembly 12. The sealing off is caused by the surface tension of the medicament forming a barrier on the membrane 42 which will prevent air present in the container 26, such as via the venting conduit 30, from being passed through to the drip chamber 16 and to the patient line 20. Thus, upon emptying of the container 26, the air present in the container will be confined to an area 39 above the membrane 42.

When a subsequent dose of medicament is required, the piercing member 28 of the spike assembly 12 is removed from the empty container 26 and attached to a full container. In order to start the flow of liquid from the subsequent container, the air confined in area 39 must be removed, and a venting membrane 36 is included in the spike assembly for this purpose. As liquid again flows from the second container 26, air will be forced out through the membrane 36. Membrane 36 is comprised of a porous hydrophobic material such as polyethylene (PE), polypropylene (PP), or polytetrafluoroethylene (PTFE), so that air is allowed to pass from area 39 to the surrounding atmosphere while preventing liquid in the funnel portion 38 from spilling through the membrane, such as in the event of an overflow condition. Once the air is removed, the roller clamp 24 is opened to allow the medicament to flow into the patient line 20. A check valve 43 prevents air from the surrounding atmosphere from entering area 39 through membrane 36 when fluid flows from the container 26.

The drip chamber 16 includes a top wall 50 providing an inlet opening 52, a bottom wall 54 providing an outlet opening 56, and at least one side wall 58 comprised of a transparent or translucent material so that medicament in the drip chamber can be readily viewed. The drip chamber 16 is preferably of cylindrical shape such that there is a single side wall 58; although other drip chamber configurations are possible and are readily contemplated by those having ordinary skill in the art. A drip orifice or opening 18 may be formed on, attached to, or may depend from the top wall 50 or, alternatively, may be formed on the outlet end 40 of the spike assembly 12. As explained above, the drip orifice 18 establishes the size of the medicament drops 59 as the medicament enters the drip chamber 16. By adjusting the rate of flow of the drops 59 into the drip chamber 16, and knowing the size of the individual drops which is dictated by the drip orifice size, a medicament dosage rate can be established. The drip chamber 16 also includes an opening or hole 60 formed in the side wall 58 and vertically displaced from the drip chamber bottom 54 by a predetermined amount "x". The opening 60 may be formed as part of a primary molding process in which the drip chamber 16 is formed, or as a secondary process wherein the opening 60 is punched-out or otherwise removed from the side wall 58. As explained more fully below, the opening 60 is dimensioned to accommodate a sealing off by of a vent plug 62 to provide a self-priming function to the drip chamber 16.

Figure 1A:
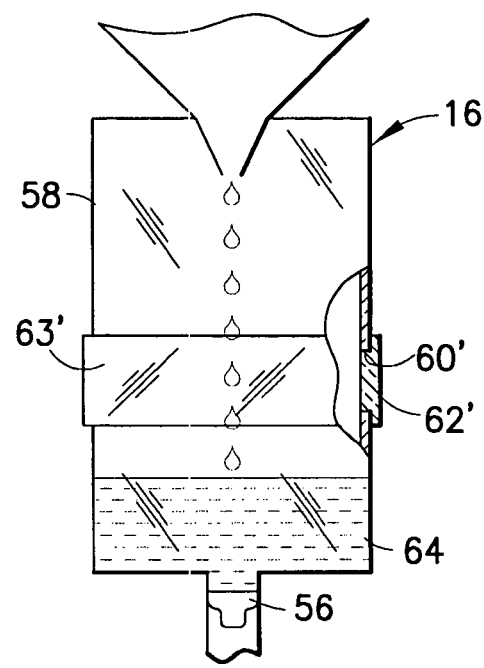
FIGS. 1a-1b are alternate embodiments of a drip chamber in accordance with the present invention.
Figure 1B:
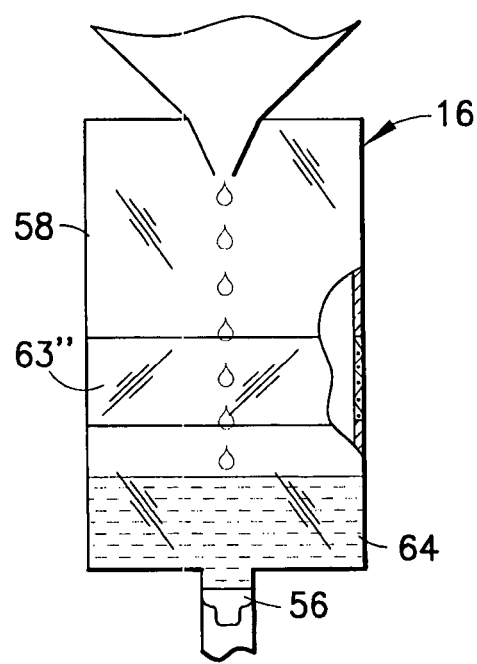

The term "vent plug" as used herein means an obstruction for sealing off the opening 60. This can be accomplished, by way of non-limiting example, by a member dimensioned for seating within the opening 60 as shown in FIG. 1 or by a cover or shield, such as a band of material 63 having a venting section 62' which is disposed about the sidewall 58 of the chamber 16 over the opening 60' as shown in FIG. 1a. Alternatively, the drip chamber side wall 58 can be integrally formed with a complete or partial band of material as shown in FIG. 1b which seals off the internal volume of the drip chamber once the band of material becomes wet, as explained below.

The medicament drops 59 form a reservoir 64 at the bottom of the drip chamber 16. The medicament is then provided to the patient line 20 for conveying the medicament to the termination end 22, at which an end cap 70 that may be detachably or permanently connected, allows coupling of the patient line to an IV needle (not shown). The end cap 70 includes a side wall 71, a front wall 73 in which a vent 72 is formed, and a termination end vent plug 74. Also disposed on the patient line 20 is the roller clamp 24 having an adjustable control such as a knurled wheel 25 for regulating the flow of liquid in the patient line 20.

A problem with existing IV systems having drip chambers lies in the setup and "priming" of the drip chamber to establish a desired or prescribed medicament flow rate at which the medicament will enter the patient. As explained above, this typically requires a heath care professional, such as a nurse, to allow the medicament in the drip chamber to reach a certain level, typically ⅓ of the drip chamber volume. In order to accomplish this, the patient line 20 needs to be obstructed or otherwise partially closed off so that the liquid will fill the drip chamber 16 at a faster rate than the liquid enters the patient line 20 to form the reservoir 64. Thus, the health care professional will be required to tighten the roller clamp 24 for this purpose. Moreover, to set the reservoir level at approximately ⅓ of the drip chamber volume, an equal volume of air in the drip chamber must be removed. In pre-existing IV systems, this was accomplished by squeezing the flexible drip chamber side wall 58. In the event the squeezing of the drip chamber side wall 58 caused an excessive amount of air to be removed, this resulted in an excessive amount of liquid collected in the reservoir 64 which then needed to be removed in a tedious manner as explained above. Also, if the liquid entered the reservoir and/or patient line too rapidly, air bubbles will be formed on the inner surface of the patient line and then have to be removed, typically by tapping the chamber 16 and/or patient line 20.

In accordance with the present invention, the manual priming activity previously performed by health care professionals can be eliminated by the IV system 10. When the spike assembly 12 is first connected to a medicament container 26, liquid will begin to flow through the liquid conduit 32 into the funnel region 38, whereupon the drip orifice 18 will cause medicament drops 59 to be formed and fall, under the force of gravity, into the drip chamber 16. To facilitate formation of the reservoir 64 and, specifically, to prevent the medicament from draining into the patient line 20 before the reservoir 64 can be formed to a desired depth relative to the drip chamber bottom 54, liquid flow through the patient line 20 must be obstructed so that the medicament level will rise in the drip chamber at a rate which exceeds the flow of the medicament into the patient line. This can be accomplished by adjustment of the roller clamp 24, such as by manipulating adjustment wheel 25 or, as is contemplated by the preferred embodiment, through the vent 72 formed in the front wall 73 of the end cap 70. Thus, if the roller clamp 24 is in its fully opened state, the narrow opening of the vent 72 will restrict liquid flow in the patient line 20 to a rate which is slower than the rate that the medicament enters the drip chamber 16 so that the reservoir 64 can form in the drip chamber and so that fluid will enter the patient line at a slow rate to prevent the formation of air bubbles therein.

With flow in the patient line 20 restricted by the roller clamp 24 and/or by the end cap 70, medicament drops 59 continue to enter the drip chamber 16 so that the reservoir 64 will rise to a height of "x". This height corresponds to the opening 60 at which the vent plug 62 is disposed. In one embodiment, the vent plug 62 is comprised of an absorptive material which allows displaced air from the drip chamber 16—which is displaced by the increased level of the reservoir 64—to pass from the drip chamber to the surrounding atmosphere but which, upon contacting liquid, expands or swells to seal off the opening 60. When this occurs, liquid in the reservoir 64 is prevented from escaping through the vent plug 62 and air from the surrounding atmosphere is prevented from re-entering the drip chamber 16 through the vent plug 62. In this manner, the IV system 10 functions as a self-priming device which automatically allows the reservoir to fill to a desired level (e.g., ⅓ of the drip chamber volume) once the spike assembly 12 is attached to the medicament container 26 so that a health care professional no longer needs to compress the drip chamber side wall 58 to cause medicament to flow therein. Because the drip chamber no longer needs to be compressed for priming, the problem of over-filling the drip chamber is avoided. Consequently, the material used to form the drip chamber 16 is no longer limited to a flexible material but can now include rigid materials.

Suitable absorptive materials for the vent plug 62 include, by way of non-limiting example, porous PE, PP, or PTFE, embedded, doped or coated with carboxymethylcellulose (CMC), polyacrylate, or other known or hereafter discovered super-absorbent polymers.

To allow air present in the patient line 20 to escape through the termination end 22 so that, upon connection of the termination end 22 to a patient, such air will not enter the patient, the termination end vent plug 74 is provided. The termination end vent plug 74 is comprised of porous PE, PP, or PTFE, embedded, doped or coated with a super-absorbent polymer and creates a barrier when liquid impinges upon it. Alternatively, the termination end vent plug 74 can be formed of a hydrophobic material. Once the patient line 20 is completely filled with medicament, all air is removed therefrom and the termination end vent plug 74 forms a barrier to prevent spillage of the medicament through the vent 72. In this state, the IV system 10 is ready for attachment to a patient IV connection. This can be accomplished by detaching the end cap from the patient line and then coupling the line to a patient. The termination end vent plug 74 allows air from the patient line 20 to pass from the patient line to the surrounding atmosphere through vent 72 in the end cap 70. However, once the termination end vent plug becomes wet through contact with the liquid in the patient line 20, air is prohibited from reentering the patient line through the vent 72.

When connecting the already-primed IV system 10 to a subsequent medicament container, the health care professional simply closes the patient line 20 via the roller clamp 24, disconnects the piercing member 28 from the empty container, and attaches it to a full container. Any amount of liquid that may exist in the piercing member 28 during disconnection and reconnection to a medicament container is de minimis and will have little effect on the level of the reservoir 64. Once connected and the patient line reopened by opening the roller clamp, air in region 39 will be removed through membrane 36 and medicament will begin to flow into the drip chamber and into the patient line 20.

Another benefit of the inventive self-priming IV system 10 is that the occurrence of a high medicament flow rate into the drip chamber is reduced or altogether avoided because the primary cause of such a condition—the manual compressing of the drip chamber side wall 58—is no longer performed. Nevertheless, to prevent the vent plug 62 from prematurely contacting the liquid medicament, such as when the medicament drops 59 enter the drip chamber 16 and cause a splatter or splashing effect against the surface of the reservoir, a splash guard 76 formed of, for example, a liquid impervious plastic shield, can be readily affixed about the vent plug 62 to the internal surface of the side wall 58 of the drip chamber. As shown, the splash guard 76 is connected to the drip chamber side wall 58 by, for example, adhesive at a location above the vent plug 62, and extends to a point below the vent plug 62 and offset from the side wall 58 so that an opening 77 is formed to allow the rising reservoir 64 to contact the vent plug 62 in an intended manner. The splashing or splattering effect can also be reduced by employing an angled outlet 40' of the spike assembly 12 (see FIG. 3) which directs high velocity or stream-like medicament formed under a high pressure condition, against the side wall 58 to reduce the speed of the medicament and, hence the creation of air bubbles in the reservoir and the occurrence of splatter.

It should be appreciated that the inventive drip chamber 16 and the vented end cap 70 can be used together in an IV system, or can be used separately, with the benefits attributed to each such feature being realized by that feature's use. For example, the drip chamber 16 can be used in conjunction with the roller clamp 24 by using the roller clamp to partially close off and restrict liquid flow in the patient line 20. This allows the reservoir 64 to fill to a desired level to moisten the vent plug 62 and also allows a slow rate of liquid to fill the patient line 20 and expel air therefrom through the termination end 22 without causing air bubbles to form on the inner surface of patient line 20. Such a system, however, still requires caregiver attention because the roller clamp 24 will need to be manipulated to adjust a desired flow rate for priming the drip chamber 16. Likewise, end cap 70 can be used at the termination end of a patient line 20 attached to any known IV delivery system, such as a system containing a drip chamber 16 or a system containing an infusion pump (not shown). The end cap 70, as explained above, will reduce the rate of liquid flow in the patient line 20 so that air bubbles will not be formed on the inner surface of the fluid conduit. Moreover, termination end vent plug 74 will prevent seepage of the liquid from the termination end 22 once the patient line becomes filled in the intended manner. If the end cap 70 is of a removable configuration, such as via a luer-type connection as is known in the art, then once the patient line 20 is filled, roller clamp 24 will be closed and end cap 70 can then be removed without causing seepage of the liquid contained in the conduit 20, whereupon the conduit can then be attached to the intravenous needle connected to a patient. Thereafter, roller clamp 24 can be re-opened to allow intended operation of the IV system.

The vent plug 62 may be constructed as a passive element which fits within or over the opening 60 or which forms a portion of the side wall 58. In a preferred embodiment, as shown in FIG. 2a, the vent plug 62 is dimensioned at its outer diameter to form a secure fit within the opening 60. The thickness of the plug 62 is dictated by the material used in forming the plug as well as in the configuration of the plug so that its intended purpose of swelling up to seal off the opening 60 for isolating the interior of the drip chamber 16 from the surrounding atmosphere is accomplished upon contact of the vent plug 62 with liquid in the reservoir 64. Suitable material for the vent plug 62 is a sintered polyethylene with an imbedded super-absorbent polymer material 63. The vent plug material may be formed in a sheet of a particular thickness, and the individual plugs 62 can then be cut or punched-out therefrom at a desired size. Alternatively, the vent plugs can be molded. The vent plug 62 can also be configured in any suitable shape such as having, for example, a round or square cross section. When in contact with liquid, such as a liquid medicament, the super-absorptive material expands or swells, closing the pores of the sintered polyethylene so that the vent plug 62 remains in a swollen state even in the event liquid is no longer in contact with it. Thus, during an "empty container" condition wherein all of the medicament has been expelled from the container 26, an increase in the vacuum level in the drip chamber 16 will tend to draw air from the surrounding atmosphere into the drip chamber 16 through the vent plug. It is required, therefore, that the vent plug remains in its swollen and engaged state within the opening 60 so that air will be prevented from entering the drip chamber 16. The vent plug is also preferably coated with an anti-bacterial agent to prevent contaminants in the surrounding atmosphere from entering the drip chamber 16 through the plug 62.

An alternative configuration of a vent plug 82 is shown in FIG. 2b as a composite of materials including a plastic housing 84 containing an amount of granular absorptive material 83 such as granular hydrogel. As shown, plug 82 has an opening 85 in communication with the drip chamber interior, and a filter or screen 88. An opposite side of the plug 82 contains a venting membrane 86 comprised of a fine mesh screen made of a plastic material. In this embodiment, screen 88 allows air evacuated from the drip chamber 16 during priming to pass through the absorptive material 83 and through venting membrane 86 to the surrounding atmosphere. As the liquid rises in the drip chamber 16, the granular hydrogel becomes wet and begins to expand. Before full expansion occurs, however, it is possible that the granular hydrogel material 83 can leech, spill, or otherwise come into contact with the reservoir 64 in the chamber 16. In this state, it is also possible for liquid to leak from the plug 82. To prevent the leeching of the granular hydrogel, the filter screen 88 is comprised of a relatively fine mesh material to maintain the hydrogel in the housing 84. Also, when wet, the venting membrane 86 provides a seal to prevent leakage, in a similar manner as membrane 42 of spike assembly 12 discussed above. Once the granular hydrogel fully expands, it seals off the opening 60 and prevents air from flowing into the chamber and liquid from flowing out of the chamber 16. The venting membrane 86 is preferably treated with an anti-bacterial agent for preventing contaminants present in the surrounding atmosphere from seeping into the drip chamber. The anti-bacterial agent can, alternatively, be incorporated as a separate permeable film, screen or antimicrobial filter 89 positioned across the drip chamber side wall opening at one end of the vent plug 82.

As shown in FIG. 2c, another configuration of a vent plug 92 includes a plastic housing 94 dimensioned for seating within the opening 60 in the side wall 58. Like the embodiment of FIG. 2b, the housing 94 can be secured in the opening 60 in any known manner. The housing 94 defines a cavity in which a formation of absorptive material 93 is disposed. An opening 95 provides an outlet for expelled air from the chamber 16 to the surrounding atmosphere. Once liquid contacts the formation 93, it causes the formation to expand and occupy the interior region of the housing 94 to thereby seal off the drip chamber 16 from the surrounding atmosphere. The formation 93 may be formed in a punch-out process from a sheet of material, or molded. As in the prior embodiments, the vent plug 93 preferably includes an anti-bacterial agent.

In yet another embodiment shown in FIG. 2d, vent plug 62 can be configured as a tube or cannula 102 having a narrow portion 107 containing an amount of absorptive material 103. A wide portion 108 connected to or integrally formed with the narrow portion 107 is disposed in and fixed to the opening 60. The wide portion 108 has an opening 105 which allows expelled air from the drip chamber 16 to communicate through the narrow portion 107 to the surrounding atmosphere. As the reservoir 64 reaches the level of the opening 60, liquid begins to flow through the narrow portion 107 and moisten the absorptive material 103 which causes the narrow portion 107 to be sealed off from the surrounding atmosphere. A venting membrane 106, similar to element 86 in FIG. 2b, is provided to prevent liquid from flowing outside of the vent plug 102. The venting membrane 106 is also preferably treated with an anti-bacterial agent to prevent outside contaminants from entering the drip chamber 16. Instead of a single cannula, two or more cannulas can be used.

Another embodiment is shown in FIG. 2e wherein a vent plug 112 is configured of a solid core 114 which is impervious to both air and liquid and which is coated with, encompassed by, or layered in, absorptive material 113. A suitable core material is PP or PE. The core 114 is affixed or secured within the opening 60. As air is expelled from the drip chamber, it passes through the absorptive material outer layer 113 and into the surrounding atmosphere. However, as liquid in the drip chamber rises and contacts the vent plug 112, the absorptive material outer layer will expand or swell to create a tight seal about the opening 60 to thereby prevent both liquid and air from further escaping from the drip chamber to the surrounding atmosphere, and also to prevent air from entering the drip chamber from the surrounding atmosphere.

In still another embodiment, the vent plug can be configured as an active device such as a mechanical valve 262 shown in FIG. 2f. As shown, mechanical valve 262 includes a housing 294 having an inlet 267 and an outlet 268 which communicate with a cavity 297 in which a float 296 is disposed. The float is preferably configured in the shape of a sphere and is formed of a buoyant material. An antimicrobial filter 269 is disposed across the outlet 268 to prevent contamination of the interior of the drip chamber 16 from the outside environment. When the reservoir level is below the inlet 267, the float 296 is spaced from the outlet 268 and allows displaced air to exit to the environment. However, when liquid enters the cavity 297, the float rises to obstruct the outlet 268 and prevents liquid from exiting from the valve 262.

Figure 3:
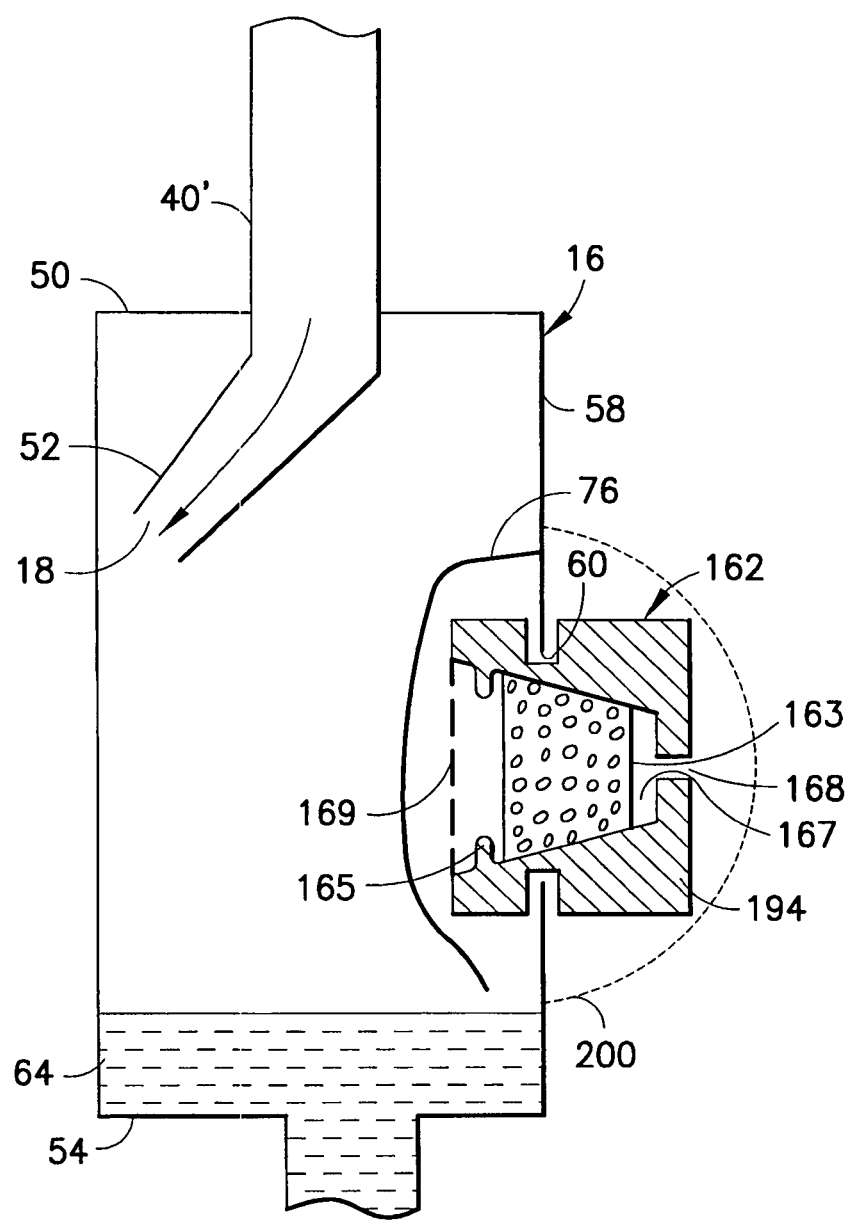
FIG. 3 depicts a partial sectional view of a vent plug affixed to a drip chamber.

Turning now to FIG. 3, a modified version of the vent plug of FIG. 2c is shown mounted in the opening 60 of the drip chamber 16. The vent plug 162 has a trapezoidal cross-section core 163 of porous absorptive material which is dimensioned for tightly fitting within a trapezoidal-shaped cavity 167 in a protective housing 194 fastened within the opening 60. An anti-bacterial membrane 169 is disposed on an inner side of the housing 194 to prevent bacteria in the surrounding atmosphere from contacting the medicament reservoir 64. As shown, the core 163 is tightly maintained at one end in the housing cavity 167 by an annular rim or by one or more posts or fingers 165, and by tapered sides of the housing 194 which form a vent hole 168 at the other end. Air exiting from the drip chamber 16 passes through membrane 169, through the pores of the core 163, and out through the vent hole 168. Once liquid contacts the core 163, however, the core material will swell or expand to close the pores to thereby seal off the interior of the drip chamber 16 from the surrounding atmosphere.

In a preferred embodiment, an outer shield 200 is attached to the side wall of the drip chamber 16 and substantially covers the vent plug 162. The outer shield 200 is comprised of a resilient transparent or translucent material, such as acrylic, PE or PP, and functions to protect the vent plug 162 from contact forces that the vent plug may otherwise encounter, such as during shipping, storage and handling of the IV system 10.

Figure 4:
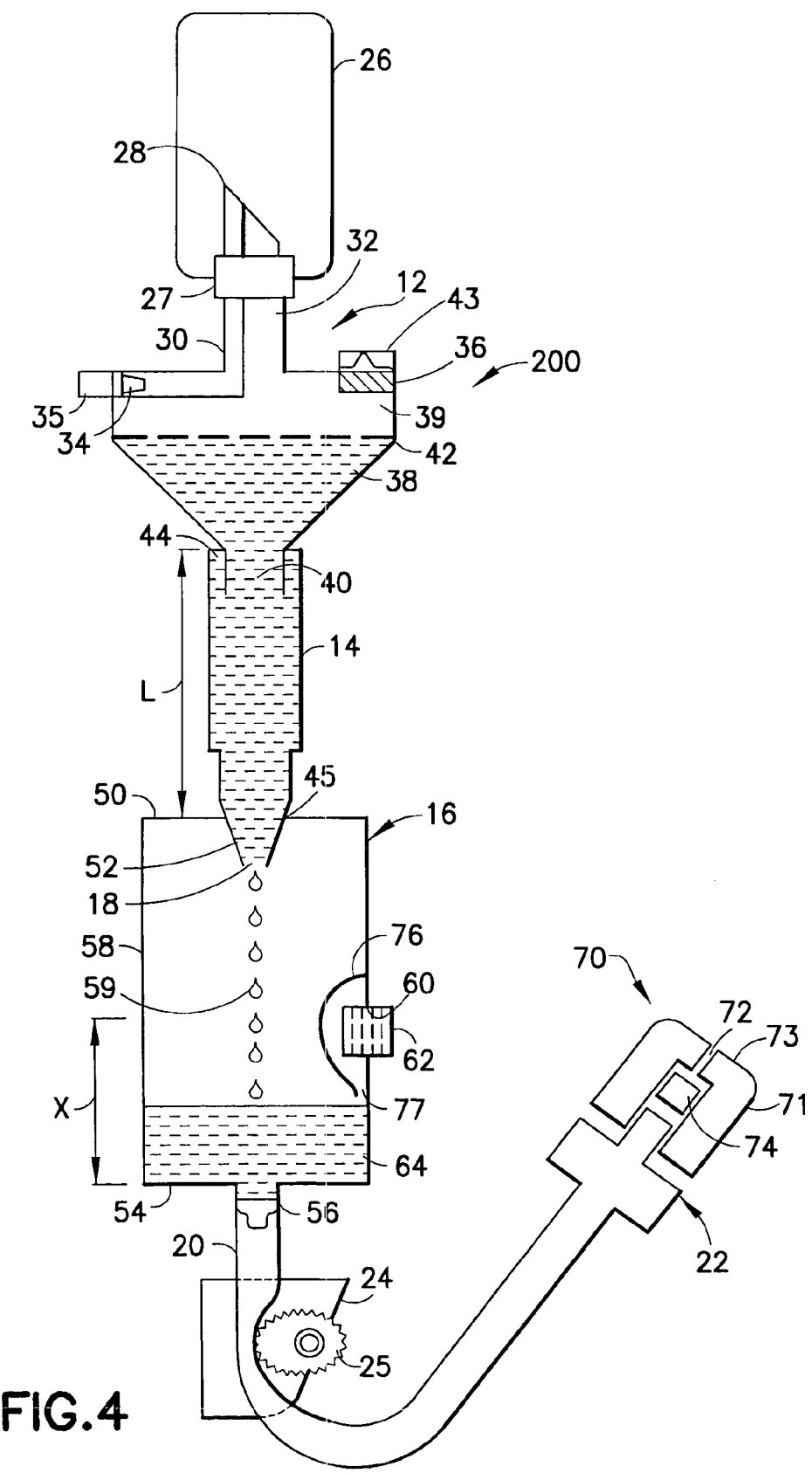
FIG. 4 is a schematic depiction of an IV system having a drip chamber coupling extension.

A further embodiment of an IV system 200 is shown in FIG. 4. Unlike the system depicted in FIG. 1, the IV system 200 does not provide a direct connection between the spike assembly 12 and the drip chamber 16. Rather, an extension conduit 14 is disposed between the spike assembly and drip chamber to transport the medicament from the spike assembly 12, and in particular, from the outlet 40 of the funnel portion 38, to the drip chamber 16. The extension conduit is comprised of a flexible tube material such as plastic, having a length "L", and which is preferably transparent or translucent. The extension conduit 14 has an inlet end 44 connected to the spike assembly outlet 40, and an outlet end 45 connected to, or otherwise disposed in, the drip chamber top wall 50. In this embodiment the drip orifice 18 may be formed in the outlet end 45 of the conduit or, may be formed in the drip chamber top wall 50. The length "L" of the conduit is sufficient to separate the relative distance between the spike assembly 12 and the drip chamber 16 so that the drip chamber is disposed at a height which is more readily viewable by the health care professional. This feature is desirable because the medicament bag or bottle may be positioned higher than the eye level of the health care professional making observation of the drip chamber and the counting of drops for flow rate adjustments will be difficult. The extension conduit 14 can be used in connection with any known IV system for separating a drip chamber from a spike assembly, including, but not limited to, the self priming IV system of FIG. 1 wherein the vent plug 62 is provided in the drip chamber 16.

Thus, while there have been shown and described and pointed out fundamental novel features of the invention as applied to a preferred embodiment thereof, it will be understood that various omissions and substitutions and changes in the form and details of the devices illustrated, and in their operation, and in the methods disclosed may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or methods shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A self-priming IV-solution delivery system for intravenous delivery of a solution from a container to a patient when the container is disposed at a height above the patient, comprising:

a coupling assembly having an input and an output, said input configured for coupling to the container to provide flow of the solution through the coupling assembly to the output;

a drip chamber having a top wall, a bottom wall, a substantially transparent side wall, an input and an output and coupled, at its input, to said coupling assembly output to receive solution drops formed from the flow of the solution for forming a reservoir defined between said bottom wall and side wall, said drip chamber side wall having an opening located at a height between said top wall and said bottom wall, and a vent plug covering said opening, said vent plug allowing air contained in said drip chamber which becomes displaced upon formation of the reservoir to escape from said drip chamber through said vent plug, said opening being oriented to permit air flow therethrough in a direction transverse to the direction of drip flow of solution from said input to said output of said drip chamber, thereby permitting the substantially unobstructed view of the drip of solution in said drip chamber; and a patient conduit coupled to said drip chamber output and having a termination end attachable to an intravenous needle of the patient for receiving a flow of solution from the reservoir, said patient conduit having a flow restriction device to restrict the flow of air and liquid in the patient conduit to allow the reservoir to attain a level at least equal to the height of said vent plug while air in the patient conduit is expelled from said termination end, wherein wetting of said vent plug by the reservoir prevents entry of air through said vent plug to said drip chamber and prevents the exit of solution from said drip chamber through said vent plug; and a termination end cap coupled to the termination end of the patient conduit and having a vent for restricting the flow of solution into the patient conduit and allowing air displaced by the flow of solution through the patient conduit to escape through the termination end, the termination end cap further comprising a termination end vent plug for preventing the escape of solution through the vent of the termination end cap and preventing the introduction of air to the patient conduit through said termination end cap upon wetting of the termination end vent plug by the solution.

2. The system of claim 1, wherein said termination end vent plug comprises a hydrophilic porous material.

3. The system of claim 1, wherein said flow restriction device further comprises a flow restriction device positioned on said patient conduit for selectively closing said patient conduit to isolate the patient from said drip chamber.

4. The system of claim 1, further comprising a flexible conduit coupled between said coupling assembly output and said drip chamber input and having a length for separating a relative distance between said drip chamber and said coupling assembly so that said drip chamber is positioned in close proximity to the patient to provide observation of said drip chamber, and to provide manipulation of said drip chamber with, at most, minimal disturbance of said coupling assembly.

5. The system of claim 1, wherein a drip orifice is located in said drip chamber top wall for forming the solution drops.

6. The system of claim 1, wherein the height of said side wall opening coincides with a reservoir level occupying approximately ⅓ of the total volume defined in said drip chamber.

7. The system of claim 1, wherein said vent plug comprises an absorbing material and a housing connected to said side wall opening and defining a cavity for receiving a formation of said absorbent material, and wherein said absorbing material comprises a super-absorbent polymer which expands in response to wetting by the reservoir.

8. The system of claim 7, wherein said vent plug further comprises an anti-bacterial agent.

9. The system of claim 7, wherein said housing cavity has a trapezoidal cross-section and wherein said formation of said super-absorbent polymer material substantially occupies said housing cavity, said housing further comprising an obstruction positioned at a housing end in communication with said drip chamber for maintaining said formation in said housing cavity.

10. The system of claim 1, wherein said vent plug comprises a housing connected to said side wall opening and defining a cavity having a first end in communication with said drip chamber, and a second end in communication with a surrounding atmosphere, said cavity receiving an amount of an absorbing material which expands in response to wetting by the reservoir, said absorbing material comprising a granular super-absorbent polymer, and further comprising a filter disposed at said first end and a venting membrane disposed at said second end.

11. The system of claim 10, wherein said vent plug further comprises an anti-bacterial agent.

12. The system of claim 1, wherein said vent plug comprises a cannula defining a cavity, and wherein an absorbing material which expands in response to wetting by the reservoir comprises an amount of super-absorbent polymer material disposed in said cavity, said cannula dimensioned for securement within said side wall opening and having a first end in communication with said drip chamber, and a second end in communication with a surrounding atmosphere.

13. The system of claim 1, wherein said vent plug comprises a rigid core of impervious material surrounded by said absorbing material which expands in response to wetting by the reservoir.

14. The system of claim 1, wherein said coupling member comprises a piercing member.

15. The system of claim 14, wherein said piercing member defines a closable venting conduit and a liquid conduit.

16. The system of claim 15, wherein said coupling assembly further comprises a funnel portion for directing solution from the container to said drip chamber.

17. The system of claim 16, wherein said coupling assembly further comprises a membrane disposed within said funnel portion for preventing air trapped above said membrane from entering said drip chamber once the container is empty.

18. The system of claim 17, wherein said coupling assembly further comprises an air filter for interfacing an area above said membrane with a surrounding atmosphere to allow air which may be trapped in said coupling member above said membrane to escape to the surrounding atmosphere.

19. The system of claim 1, wherein said coupling member comprises an output end defining a drip orifice for forming the solution drops.

20. The system of claim 1, further comprising an outer shield connected to said side wall above said vent plug in an exterior of said drip chamber and extending across said vent plug.

21. The solution delivery system of claim 1, wherein said termination end cap allows the formation of said reservoir in said drip chamber while simultaneously permitting the escape of air from said conduit through said termination end cap.

22. A self-priming IV-solution delivery system for intravenous delivery of a solution from a container to a patient when the container is disposed at a height above the patient, comprising:

a coupling assembly having an input and an output, said input configured for coupling to the container to provide flow of the solution through the coupling assembly to the output;

a drip chamber having a top wall, a bottom wall, a substantially transparent side wall, an input and an output and coupled, at its input, to said coupling assembly output to receive solution drops formed from the flow of the solution for forming a reservoir defined between said bottom wall and side wall, said drip chamber side wall having an opening located at a height between said top wall and said bottom wall, and a vent plug covering said opening, said vent plug allowing air contained in said drip chamber which becomes displaced upon formation of the reservoir to escape from said drip chamber through said vent plug, said opening being oriented to permit air flow therethrough in a direction transverse to the direction of drip flow of solution from said input to said output of said drip chamber, thereby permitting the substantially unobstructed view of the drip of solution in said drip chamber;

a patient conduit coupled to said drip chamber output and having a termination end attachable to an intravenous needle of the patient for receiving a flow of solution from the reservoir, said patient conduit having a flow restriction device to restrict the flow of air and liquid in the patient conduit to allow the reservoir to attain a level at least equal to the height of said vent plug while air in the patient conduit is expelled from said termination end, wherein wetting of said vent plug by the reservoir prevents entry of air through said vent plug to said drip chamber and prevents the exit of solution from said drip chamber through said vent plug;

a splash guard connected to said side wall above said vent plug in an interior of said drip chamber and extending across said vent plug; and a termination end cap coupled to the termination end of the patient conduit and having a vent for restricting the flow of solution into the patient conduit and allowing air displaced by the flow of solution through the patient conduit to escape through the termination end, the termination end cap further comprising a termination end vent plug for preventing the escape of solution through the vent of the termination end cap and preventing the introduction of air to the patient conduit through said termination end cap upon wetting of the termination end vent plug by the solution.

23. In an IV-solution delivery system for intravenous delivery of a solution from a container to a patient when the container is disposed at a height above the patient, having a coupling assembly with an input and an output, said input configured for coupling to the container to provide flow of the solution through the coupling assembly to the output, a drip chamber having a top wall, a bottom wall, a substantially transparent side wall, an input and an output and coupled, at its output, to said coupling assembly to receive solution drops formed from the flow of the solution for forming a reservoir defined between said bottom wall and side wall, and a patient conduit coupled to said drip chamber output and having a termination end attachable to an intravenous needle of the patient for receiving a flow of solution from the reservoir, the improvement providing a self-priming of the solution delivery system and comprising:

an opening formed in said drip chamber side wall at a height between said top wall and said bottom wall, and a vent plug covering said opening, said vent plug comprised of a material for allowing air contained in said drip chamber which becomes displaced upon formation of the reservoir to escape from said drip chamber through said vent plug, said opening being oriented to permit air flow therethrough in a direction transverse to the direction of drip flow of solution from said input to said output of said drip chamber, thereby permitting the substantially unobstructed view of the drip of solution in said drip chamber;

said patient conduit having a flow restriction device to restrict the flow of air and liquid in the patient conduit to allow the reservoir to attain a minimum level at least equal to the height of said vent plug while air in the patient conduit is expelled from said termination end, wherein wetting of said vent plug by the reservoir prevents entry of air through said vent plug to said drip chamber and prevents the exit of solution from said drip chamber through said vent plug; and a termination end cap coupled to the termination end of the patient conduit and having a vent for restricting the flow of solution into the patient conduit and allowing air displaced by the flow of solution through the patient conduit to escape through the termination end, the termination end cap further comprising a termination end vent plug for preventing the escape of solution through the vent of the termination end cap and preventing the introduction of air to the patient conduit through said termination end cap upon wetting of the termination end vent plug by the solution.

24. The improvement of claim 23, wherein said vent plug comprises a super-absorbent polymer material which swells in response to wetting by the reservoir.

25. The system of claim 24, wherein said vent plug comprises a housing connected to said side wall opening and defining a cavity for receiving a formation of said super-absorbent polymer material.

26. The system of claim 25, wherein said housing cavity has a trapezoidal cross-section and wherein said formation of super-absorbent polymer material substantially occupies said housing cavity, said housing further comprising an obstruction positioned at a housing end in communication with said drip chamber for maintaining said formation in said housing cavity.

27. The system of claim 24, wherein said vent plug comprises a housing connected to said side wall opening and defining a cavity having a first end in communication with said drip chamber, and a second end in communication with a surrounding atmosphere, said cavity receiving an amount of said super-absorbent polymer material in a granular form, and further comprising a filter disposed at said first end and a venting membrane disposed at said second end.

28. The system of claim 24, wherein said vent plug comprises a cannula defining a cavity and containing an amount of said super-absorbent polymer material therein, said cannula dimensioned for securement within said side wall opening and having a first end in communication with said drip chamber, and a second end in communication with a surrounding atmosphere.

29. The system of claim 23, wherein said vent plug comprises a rigid core of impervious material surrounded by a layer of super-absorbent polymer material.

30. A method of intravenous delivery of a solution from a container to a patient, comprising the steps of disposing the container at a height above the patient;

attaching a coupling assembly to said container for providing flow of the solution from the container;

coupling a drip chamber having a bottom wall, a substantially transparent side wall, an input, an output, an opening in the side wall, and a vent plug disposed over said opening, to said coupling assembly to receive solution drops formed from the flow of the solution, said opening being oriented to permit flow therethrough in a direction transverse to the direction of drip flow of solution from said input to said output of drip chamber, thereby permitting the substantially unobstructed view of the drip of solution in said drip chamber;

connecting a patient conduit to said drip chamber output, said patient conduit having a termination end and a termination end cap coupled thereto, said termination end cap having a vent for restricting the flow of solution into said patient conduct and allowing air displaced by the flow of solution through said patient conduit to escape through said termination end, said termination end cap further comprising a termination end vent plug for preventing the escape of solution through said vent of said termination end cap and preventing the introduction of air to said patient conduit through said termination end cap;

restricting the flow of solution in said patient conduit to a rate below the rate of solution entering said drip chamber to allow a reservoir defined between said bottom wall and side wall to form to a height for wetting said vent plug, said vent plug allowing air contained in said drip chamber which becomes displaced upon formation of the reservoir to escape from said drip chamber through said vent plug;

connecting a termination end of said patient conduit to the patient once the vent plug is wet from the reservoir, air is removed from the patient conduit and said termination cap vent plug is wet; and discontinuing said restriction step upon wetting of said vent plug by said reservoir, removal of air from said patient conduit, and wetting said termination cap vent plug.

31. The method of claim 30, wherein said restricting step comprises closing a clamp disposed on said patient conduit.

32. A self-priming IV-solution delivery system for intravenous delivery of a solution from a container to a patient when the container is disposed at a height above the patient, the system comprising:

a coupling assembly having an input and an output, said input configured for coupling to the container to provide flow of the solution through said coupling assembly to said output;

a drip chamber having a top wall, a bottom wall, a substantially transparent side wall, an opening in said side wall, an input and an output and coupled, at its input, to said output of said coupling assembly to receive drops of the solution formed from the flow of the solution through said output of said coupling assembly, thereby forming a reservoir defined between said bottom wall and said side wall, said opening being oriented to permit air flow therethrough in a direction transverse to the direction of drip flow of solution from said input to said output of said drip chamber, thereby permitting the substantially unobstructed view of the drip of solution in said drip chamber;

a drip chamber vent plug covering said opening in said drip chamber, said drip chamber vent plug allowing air contained in said drip chamber which becomes displaced upon formation of said reservoir to escape from said drip chamber through said drip chamber vent plug, said drip chamber vent plug being formed at least partly by a wettable material which seals upon wetting, so that wetting of said drip chamber vent plug prevents entry of air through said drip chamber vent plug into said drip chamber and prevents the exit of solution from said drip chamber through said drip chamber vent plug;

a patient conduit coupled to said drip chamber output and having a termination end attachable to an intravenous needle that may be attached to the patient for receiving a flow of solution from said reservoir and dispensing that flow to the patient;

a termination end cap at said termination end of said patient conduit, said termination end cap including a termination end vent for allowing air entrapped in said patient conduit prior to use to be purged from said patient conduit before the solution is introduced to the patient, said termination end cap having a termination end vent plug for allowing air present in said patient conduit to pass through said termination end vent and for preventing leakage of solution from said termination end cap, said termination end vent plug being formed at least partly by a wettable material which seals upon wetting, so that wetting of said termination end vent plug by the solution flowing through said conduit prevents the exit of solution from said patient conduit through said termination end cap and prevents reintroduction of air through said termination end cap to said patient conduit; and wherein said drip chamber vent plug and said termination end cap cooperate to allow the formation of said reservoir to proceed while purging of said entrapped air from said patient conduit until at least one of said drip chamber vent plug and said termination end vent plug is wetted and thereby sealed.

* * * * *